United States Patent [19]
Freyermuth et al.

[11] 3,956,313
[45] May 11, 1976

[54] N-(SUBSTITUTED-THIOMETHYL)-2-PYRROLIDINONES

[75] Inventors: Harlan B. Freyermuth; David I. Randall, both of Easton, Pa.

[73] Assignee: GAF Corporation, New York, N.Y.

[22] Filed: Apr. 13, 1970

[21] Appl. No.: 28,010

[52] U.S. Cl. .......................................... 260/326.5 S
[51] Int. Cl.[2] ........................................ C07D 207/26
[58] Field of Search .............................. 260/326.5 S

[56] References Cited
UNITED STATES PATENTS
3,228,955    1/1966    Hickner .............................. 260/307

*Primary Examiner*—Joseph A. Narcavage
*Attorney, Agent, or Firm*—Walter C. Kehm; Joshua J. Ward

[57] ABSTRACT

N-(Substituted-thiomethyl)-2-pyrrolidinones of the structural formula:

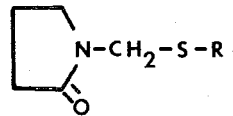

wherein R represents hydrocarbon or substituted hydrocarbon groups such as alkyl, aryl, alkenyl, alkynyl, cycloalkyl, aralkyl and alkaryl, are useful as organic solvents and dyestuff intermediates. They are prepared by the reaction of N-hydroxymethyl-2-pyrrolidinone with a hydrocarbyl or substituted hydrocarbyl mercaptan in the presence of an acid catalyst.

3 Claims, No Drawings

N-(SUBSTITUTED-THIOMETHYL)-2-PYRROLIDI-NONES

BACKGROUND OF THE INVENTION

1. Field of the Invention

This invention relates to N-(substituted-thiomethyl) derivatives of N-hydroxymethyl-2-pyrrolidinone and methods for their production.

2. Description of the Prior Art

N-hydroxymethyl pyrrolidinone is a compound known in the art as an intermediate in the preparation of dyestuffs. As taught in U.S. Pat. No. 3,073,843, this material is prepared by the reaction of pyrrolidinone and formaldehyde or a precursor of formaldehyde. This patent does not suggest the formation of derivatives of this compound however. In addition, Chemical Abstracts, Volume 55, page 27267H (1961) discloses the reaction of N-chloromethyl-2-pyrrolidinone with a mixture of sodium methylate and methanol to yield 64% of N-methoxymethyl-2-pyrrolidinone. Also, Chemical Abstracts, Volume 54, page 1286f (1960) teaches that N-chloromethyl-2-pyrrolidinone can be prepared in 87% yield by treatment of the methylol derivative with SOCl$_2$ in benzene solvent at 8°C.

In none of these prior art teachings, however, are there suggestions for preparation of thiomethyl derivatives of N-hydroxy methyl pyrrolidinone which are useful as organic solvents.

SUMMARY OF THE INVENTION

It is accordingly one object of the invention to provide substituted thiomethyl derivatives of N-methyl-2-pyrrolidinone.

A further object of the invention is to provide N-(substituted thiomethyl)-2-pyrrolidinones useful as organic solvents.

A still further object of the invention is to provide methods for preparation of N-(substituted thiomethyl)-2-pyrrolidinones.

Other objects and advantages of the present invention will become apparent as the description thereof proceeds.

In satisfaction of the foregoing objects and advantages there are provided by this invention derivatives of N-methyl-2-pyrrolidinones which have the following structural formula:

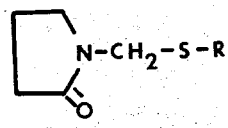

wherein R is a hydrocarbon group or a substituted hydrocarbon group, and methods for their production.

DESCRIPTION OF PREFERRED EMBODIMENTS

As indicated above, this invention is concerned with derivatives of N-hydroxymethyl-2-pyrrolidinone which are useful as organic solvents and in other areas.

These novel products have the following general structural formula:

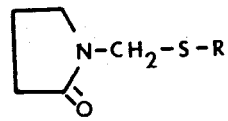

wherein R is a hydrocarbon or substituted hydrocarbon group.

Representative hydrocarbon groups for R include the following:

a. Alkyl groups and substituted alkyl groups of 1 to about 18 carbon atoms, either straight or branched chained, e.g. methyl, ethyl, n-propyl, isopropyl, n-butyl, isobutyl, n-pentyl, n-hexyl, nonyl, decyl, dodecyl, hydroxyalkyl, e.g. hydroxymethyl, 2-hydroxyethyl, 3-hydroxypropyl, haloalkyl, e.g. 2-chloropropyl, 2-chloroethyl, 3-chloropropyl, etc. and the like, as well as unsaturated carbon chains such as alkenyl (e.g. ethenyl, propenyl, etc.) and alkynyl (e.g. propynyl, butynyl, etc.);

b. Cycloalkyl groups of 3 to about 8 carbon atoms such as cyclopropyl, cyclobutyl, cyclopentyl, cyclohexyl, cycloheptyl and cyclooctyl;

c. Aryl groups and substituted aryl groups (e.g. alkaryl) of about 6 to about 15 carbon atoms, e.g. phenyl, o-, m- and p-xylyl, tolyl, phenyl substituted by one or more alkyl groups of 1 to 7 carbon atoms, 1-naphthyl, 2-naphthyl and the like; and d. Aralkyl groups such as benzyl, phenethyl and the like.

As indicated above, the products of this invention have various uses. Thus they are good organic solvents, especially those which contain an alcohol moiety and a lactam moiety. They are particularly good solvents for polymers, such as vinyl chloride polymers and copolymers, polyamides, polyacrylates, polyvinyl alcohol, etc. as well as for herbicides, insecticides, fungicides and the like. In addition the compounds containing a —CH$_2$CH$_2$OH group can be converted to the sulfone by the process described in U.S. Pat. No. 3,006,963 and can then be applied to cotton and other cellulosics in order to animalize the cotton and thus make it responsive to acid dyes as described in U.S. Pat. No. 3,100,131. further the compounds of the invention are useful in biological applications and as dyestuff intermediates. Also when the R group is a long chain alkyl group or an alkyl benzene group the products have interesting properties as surfactants, the alkyl or alkyl benzene group being an hydrophobic group and the lactam group being an hydrophillic group so that the products have the proper hydrophobichydrophillic balance to be useful as surface active agents.

The products of this invention may be prepared by the reaction of N-hydroxymethyl-2-pyrrolidinone (prepared as described in U.S. Pat. No. 3,073,843 by the reaction of 2-pyrrolidinone with formaldehyde or a formaldehyde-liberating substance in the presence of an alkaline catalyst) with a mercaptan of the formula:

R—SH wherein R is as defined above. Preferred mercaptans for use in this invention within the scope of the above formula are 2-mercaptoethanol, tridecylmercaptan, methyl mercaptan, ethyl mercaptan, n-propyl mercaptan, octadecyl mercaptan, nonyl mercaptan, hydroxymethyl mercaptan, cyclohexyl mercaptan, phenyl mercaptan, tolyl mercaptan, 2- or 3-chloropropyl mercaptan, 2-chloroethyl mercaptan, 1-naphthyl mercaptan, 2-naphthyl mercaptan, benzyl mercaptan, phenethyl mercaptan and the like.

The reaction is conducted by contacting the N-hydroxy-methyl-2-pyrrolidinone and mercaptan in substantially stoichiometric ratios in the presence of an acid catalyst. The acid catalyst is employed in an amount of about 1 to 50% by weight of the two primary reactants and may be either an inorganic acid, an organic acid or mixtures thereof. Suitable acid catalysts which may be used include mineral acids such as hydrochloric acid, sulfuric acid, phosphoric acid, phosphonic acid, nitric acid and the like. Organic acid catalysts which may be used include acetic acid, para-toluene sulfonic acid, benzenesulfonic acid, methanesulfonic acid, trichloroacetic acid and the like.

The reaction is conducted by charging the 2-pyrrolidinone and mercaptan to a reaction flask and agitating until a substantially homogeneous mixture is obtained at about room temperature. A solvent for the reactants is not necessary but an inert solvent can be utilized if desired. Then with cooling, the acid catalyst is added gradually and the resulting mixture thereafter agitated for about 1-5 hours at room temperature (i.e. about 20°-50°C.), and then agitated with water bath cooling for a short time. The resulting mixture is then neutralized to take care of the excess acid by the gradual addition of a base, preferably about a 10-60% aqueous solution of an alkali metal hydroxide, (e.g. NaOH, KOH or LiOH), or an alkaline earth metal hydroxide. Also alkaline earth metal or alkali metal oxides, carbonates or bicarbonates may be used for the neutralization as well as mixtures of bases.

After neutralization, the excess liquid is removed as by evaporation and the product recovered by conventional methods as by distillation. Yields from this reaction run generally about 70-90% of theory.

The following examples are provided to illustrate the products and processes of the invention but it is not to be considered as limited thereto.

EXAMPLE I

A 500 ml. 3-necked flask equipped with a stirrer, thermometer and condenser was charged with 115 grams (1 mole) of N-hydroxymethyl-2-pyrrolidinone and 78 grams (71 ml.; 1 mole) of 2-mercaptoethanol. The mixture was stirred for about 2 hours, during which time the mixture became homogeneous. With cooling by a water bath, 50 grams (42 ml.) of concentrated hydrochloric acid (sp. g. 1:192) was added dropwise during a 15-20 minute period. The mixture was then stirred at room temperature for 2 hours, and then, with cooling by a water bath, the acid was neutralized by the gradual addition of 40 grams (26 ml.) of a 50% sodium hydroxide solution to a pH 9.8. The reaction mixture was then stripped by a rotary flask evaporator using steam heat and the house vacuum. Precipitated salt was filtered off. The residue was placed in a distillation flask equipped with a 3 × ¾ Vigreaux column and a still head. The fraction distilling at 140°-142°C./0.15 mm. was collected ($n_D^{25}$ 1.54000). The product has the following composition:

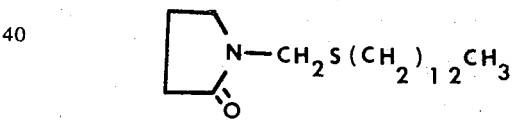

| For $C_7H_{13}NSO_2$ | Calcd. | Found |
|---|---|---|
| % N | 8.0 | 8.02 |
| % S | 18.3 | 18.27 |

EXAMPLE II

A 250 ml. 3flask equipped with a stirrer, thermometer and condenser was charged with 20.0 grams (0.25 mole) of N-hydroxymethyl-2-pyrrolidinone and 54 grams (64 ml.; 0.25 mole) of tridecylmercaptan. The mixture was stirred for 2 hours, then with cooling, 12.5 grams (10.5 ml.) of concentrated hydrochloric acid (sp. g. 1.192) was added dropwise at room temperature. The mixture was then stirred at room temperature for 2 hours. The hydrochloric acid was neutralized at room temperature (with cooling) by the gradual addition of 10 grams (6.5 ml.) of a 50% sodium hydroxide solution to a pH 9.0. The mixtue was then placed on a rotary flash evaporator using steam heat and the vacuum of the house line for several hours. The precipitated salts were filtered off in a Buchner funnel and the salt cake was washed with benzene (50 ml.). The filtrate was returned to the rotary flash evaporator and the moisture and benzene further stripped under steam heat and the vacuum of an electric pump. The residue weighed 56.7 grams ($n_D^{25}$ 1.4850). The product has the following structure:

| For $C_{18}H_{35}NSO$ | Calcd. | Found |
|---|---|---|
| % N | 4.47 | 4.49 |
| % S | 10.04 | 9.96 |

EXAMPLE III

The reaction of Example I was repeated except that the mercaptan used was phenyl mercaptan and the catalyst was p-toluene sulfonic acid. Using the same reaction conditions and work-up procedure there was obtained a 78.5% yield of a product of the following composition:

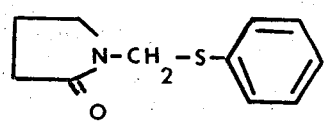

EXAMPLES IV–VIII

The reaction of Example I was repeated except that the mercaptans employed in each case were as follows:
- IV. Methyl mercaptan
- V. n-Butyl mercaptan
- VI. Benzyl mercaptan
- VII. Cyclohexyl mercaptan
- VIII. Propargyl mercaptan In every case, good yields of the corresponding substituted thiomethyl-2-pyrrolidinone were obtained.

By reaction with alkali, the pyrrolidone ring is opened to yield derivatives of γ-(N-substituted mercaptomethyl) amino butyric acid.

The invention has been described herein with reference to certain preferred embodiments. However, the invention is not to be considered as limited thereto as variations thereon will become obvious to those skilled in the art.

What is claimed is:

1. A compound of the formula

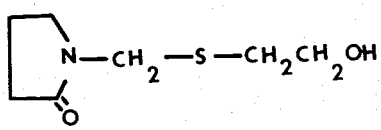

2. A process for the preparation of a compound of the formula:

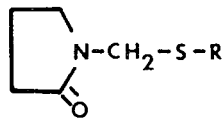

wherein R is selected from the group consisting of methyl, ethyl, n-propyl, isopropyl, n-butyl, isobutyl, n-pentyl, n-hexyl, nonyl, decyl, dodecyl, hydroxymethyl, 2-hydroxyethyl, 3-hydroxypropyl, chloromethyl, ethenyl, propenyl, propargyl, butynyl, cyclopropyl, cyclobutyl, cyclopentyl, cyclohexyl, cycloheptyl, cyclooctyl, phenyl, tolyl, o-, m- and p-xylyl, 1-naphthyl, 2-naphthyl, benzyl and phenethyl, which comprises reacting N-hydroxymethyl-2-pyrrolidinone with a mercaptan of the formula:

R—SH wherein R is as described above, in the presence of an acidic catalyst and at a temperature of from about 20°C to about 50°C.

3. A process according to claim 2 wherein the acid catalyst is selected from the group consisting of mineral acids and organic acids.

* * * * *